United States Patent [19]

Wilkins

[11] Patent Number: 4,813,424
[45] Date of Patent: Mar. 21, 1989

[54] LONG-LIFE MEMBRANE ELECTRODE FOR NON-IONIC SPECIES

[75] Inventor: Ebtisam S. Wilkins, Rockville, Md.

[73] Assignee: University of New Mexico, Albuquerque, N. Mex.

[21] Appl. No.: 137,228

[22] Filed: Dec. 23, 1987

[51] Int. Cl.⁴ .................................................. A61B 5/00
[52] U.S. Cl. ...................................... 128/635; 204/400; 435/15
[58] Field of Search ......................... 128/635, 639–642, 128/632; 204/400, 414, 416, 418–419, 1 T; 435/15

[56] References Cited

U.S. PATENT DOCUMENTS

| | | | |
|---|---|---|---|
| 4,109,648 | 8/1978 | Larke et al. | 128/639 |
| 4,115,209 | 9/1978 | Freiser et al. | 204/1 T |
| 4,273,135 | 6/1981 | Larimore et al. | 128/640 |
| 4,340,457 | 7/1982 | Kater | 128/635 X |
| 4,352,359 | 10/1982 | Larimore et al. | 128/640 |
| 4,440,175 | 4/1984 | Wilkins | 128/635 |
| 4,554,924 | 11/1985 | Engel | 128/640 |
| 4,650,547 | 3/1987 | Gough | 128/635 X |
| 4,653,499 | 3/1987 | Murray, Jr. et al. | 128/635 |
| 4,706,678 | 11/1987 | Otten et al. | 128/635 |

*Primary Examiner*—Max Hindenburg
*Assistant Examiner*—Angela D. Sykes
*Attorney, Agent, or Firm*—Albert Sopp

[57] ABSTRACT

An improved membrane electrode for measuring the concentration of a non-ionic species in an essentially aqueous medium comprising:
an electrically conductive substrate;
a first coating surrounding said substrate composed of a mixture of polymeric material, an anion exchange material, and a water-insoluble alkaline earth metal salt of said non-ionic species, and
a hydrogel coating of material surrounding said first coating having a positive charge of sufficient potential to prevent leaching of the substantial amounts of the alkaline eath metal component of said salt.

10 Claims, 1 Drawing Sheet

LONG-LIFE MEMBRANE ELECTRODE FOR NON-IONIC SPECIES

This invention relates to membrane electrodes and more particularly to an improved electrode for protracted use in potentiometric and polarographic assays for non-ionic species such as glucose, fructose, and similar materials.

Specifically, the present invention provides an improvement enabling longer useful life and stability of the membrane electrode arrangement set forth in my U.S. Pat. No. 4,440,175 issued Apr. 3, 1984 (the "'175 patent"). The membrane described in the '175 patent is particularly suitable for glucose concentration measurement, and provides a potentiometric or polarographic response which represents a direct measurement of the glucose concentration. When the membrane component is formed of a blood-compatible polymeric material, the electrode is suitable for implantation within the body for continuous in vivo monitoring of the concentration of glucose or other non-ionic species in the blood or interstitial fluid for protracted periods.

In essence, the arrangement described in the '175 patent comprises a coated wire membrane electrode generally similar to the type described in U.S. Pat. No. 4,115,209 to Freiser et al issued Sept. 19, 1978, wherein, according to the '175 patent, the polymeric matrix of the membrane component of the electrode comprises a suitable polymer (see '175 patent, col. 3, line 8–17), and the anion exchange material comprises a quaternary ammonium salt such as tricaprylyl methyl ammonium chloride commercially available under the trade name Aliquat 336S, and the non-ionic species present in the membrane component of the electrode comprises a water insoluble salt. As mentioned in the '175 patent, col. 3, lines 30–34, water soluble salts are totally unsatisfactory, and a suitable water-insoluble salt is preferably an alkaline earth metal salt such as barium salts. Of course, the terms water soluble and water-insoluble as applied to salts are relative terms. Water-insoluble salts do exhibit some water solubility, and to the extent there is water solubility in such a salt, there is a reduction in the useful life of the membrane electrode because of leaching.

Of course, in the situation where the membrane arrangement is employed in vivo, say, as a glucose sensor, the useful life of the membrane is a more critical factor. For example, if the glucose sensor comprises part of an insulin delivery system implanted in a patient for in vivo operation, the useful life of the system in vivo would be limited by the life of the sensor dependent upon the water solubility of its membrane electrode.

SUMMARY OF THE INVENTION

A primary object of the present invention is to provide a membrane electrode having improved stability, prolonged useful life, and quicker response.

It is another object of the present invention to provide an improved membrane electrode sensor having an extended, useful, operational life for use in vivo to monitor concentration of glucose or similar materials in blood or interstitial fluid and to provide signals representing such concentration for monitoring or for use as feedback control in an implanted insulin delivery system.

The above and other objects of the invention are accomplished by providing a membrane electrode having a salt substantially more water-insoluble than the brium glucose salt described in Example 1 of the '175 patent and a positively charged coating on the sensor membrane matrix which prevents leaching of barium.

DESCRIPTION OF THE PREFERRED EMBODIMENTS

Figure 1:
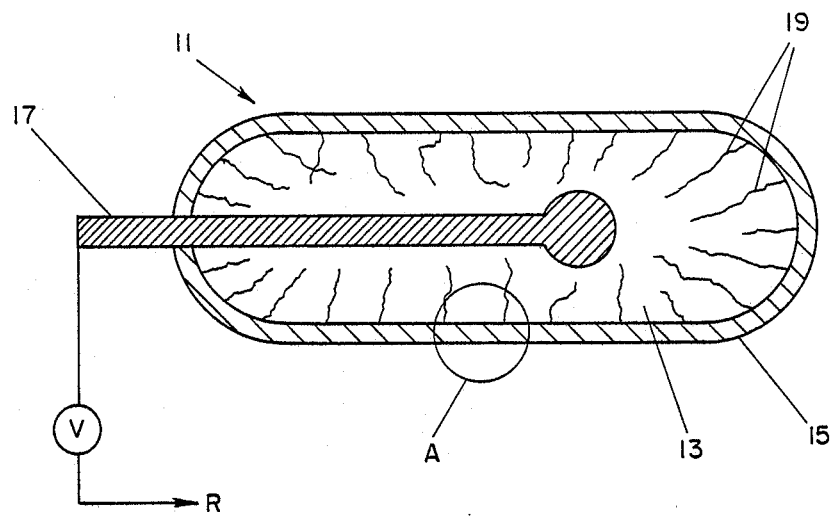
FIG. 1 is a longitudinal cross section of a sensing probe and membrane arrangement according to an embodiment of the invention.
Figure 2:
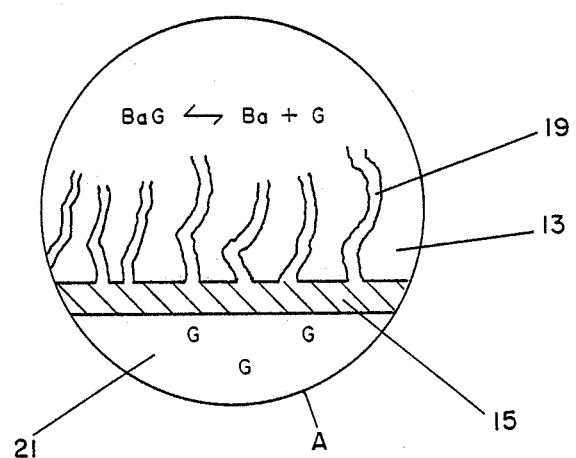
FIG. 2 is an expanded view of section A of the embodiment of FIG. 1.

The arrangement according to an embodiment of the invention is generally shown in FIGS. 1 and 2 as a membrane electrode or sensor probe 11 having a porous membrane matrix 13 and a positively charged hydrogel coating 15 surrounding the matrix. The matrix 13 is a mix of several materials including, as described in my '175 patent, a polymeric material, an anion exchange material, and a water-insoluble salt of the non-ionic species to be measured. The polymeric material may be any suitable polymer, including, for example, vinyl polymers, including polyvinyl chloride, polyvinylidene chloride, polyethylene, polypropylene, polybutadiene, polyacrylamides, polyacrylates, polyvinyl acetate, chloroprene, polystyrenes, polyacrylonitrile, and the like; condensation polymers, such as polyamides, polycarbonates, polyurethanes, polyesters, polyethers, and the like; and natural resins such as purified natural rubber. For body implantation, the polymer should be one exhibiting good blood compatibility.

The polymeric matrix 13 surrounds an electrically conductive substrate wire 17 such as gold, copper, carbon, silver, or the like and has pores 19. The matrix is further comprised of both anion exchange salts and a water-insoluble, non-ionic salt. The anion exchange material of the membrane component may suitably be, for example, a quaternary alkyl, aryl, or aralkyl ammonium phosphonium, arsonium, stibonium or sulfonium salt. Preferably, the anion exchange material is a quaternary ammonium salt, such as, for example, tricaprylyl methyl ammonium chloride, commercially available under the trade name Aliquat 336S.

The water insoluble non-ionic salt portion of the matrix 13 is preferably an alkaline earth metal salt specifically formulated and prepared in an improved arrangement in accordance with this invention such as is described in the Example. This salt is generally indicated in FIG. 2 as a barium-glucose complex—BaG. By proper selection of the non-ionic species portion of the water-insoluble salt, the membrane electrode of the present invention can be rendered sensitive to any particular non-ionic species for which measurement is desired. This is shown in FIG. 2 in the area 21 as glucose material G. in fluid outside coating 15. While the membrane electrode has been found to be particularly suitable for use in measuring glucose concentration, its applicability extends to a wide range of other non-ionic species, including, for example, fructose, creatine, creatinine, glycogen, and the like.

The membrane matrix 13 will generally include the anion exchange material in amounts ranging from about 1 to about 25% by weight, and preferably from about 10 to about 25% by weight. The molar ratio of the anion exchange material to the water-insoluble salt of the non-ionic species will generally range from about 1:1 to about 3:1, with about 2:1 being preferred. One or more plasticizers for the polymer, compatible with the polymer, the anion exchange material, and the water-insoluble salt, may be included within the membrane to attain a more homogenous mixture of the components thereof. Suitable plasticizers which may be used, alone or in combination, depending upon the particular polymer employed, include cyclohexanone, dioctyl phosphonate, tributyl phosphate, isoamyl alcohol, n-decanol, diphenylphthalate, dioctylphthalate, and diphenylphthalate. When a plasticizer is used, it will generally be employed in an amount ranging from about 10 to about 50% by weight of the membrane.

The membrane matrix 13 may suitably by prepared or fabricated by first forming a homogenous solution of the aforementioned materials—the polymer, the anion exchange material, the water-insoluble salt of the non-ionic species, and a plasticizer—which are blended in a suitable organic solvent, such as, for example, an alcohol (e.g., isoamyl alcohol, benzyl alcohol, or decanol), a ketone (e.g., cyclohexanone), an ester (e.g., methyl acetate, or tributyl phosphate), a cyclic ether (e.g., tetrahydrofuran), or mixtures thereof. Such solution is then either cast or coated onto a suitable substrate, depending upon the type of electrode being prepared, and the solvent is then evaporated.

In the membrane electrode of the present invention, the membrane matrix 13 is first formed as a layer (e.g., coated or laminated) on the conductive substrate 17. Any suitable conductive substrate can be employed, such as, for example, a wire made of platinum, silver, gold, copper, carbon, or the like. Noble metals are particularly suitable as conductive substrates. The membrane is preferably formed as a coating directly on the conductive substrate 17 by a succession of dip and evaporation steps.

Next, the coating 15 is added to surround the matrix 13. The coating 15 comprises a porous hydrogel bearing a positive electrical charge which repels the positively charged barium component of the salt, thereby reducing leaching of the barium from the matrix 13. The preparation and composition of the hydrogel coating 15 is set forth in the example.

Before use, the membrane electrode of the present invention should suitably be conditioned by soaking in a dilute solution of the non-ionic species for which it is sensitive (e.g., for two to three hours, depending on the thickness of the membrane), and stored in such conditioning solution when not in use.

The membrane electrode of the present invention may suitably be employed, in accordance with conventional assaying techniques well known in the art, for direct potentiometric or polarographic assays for measuring the concentration of a given non-ionic species as various aqueous test solutions, including body fluids such as blood, plasma, serum, urine and the like. The electrodes are particularly suitable for use in providing a direct measurement of glucose concentration in blood or other body fluids, and are suitable for being implanted within the body for continuous in vivo monitoring of such glucose concentration. If necessary to achieve a response, the electrode may be biased by an applied small voltage generated by an external source of EMF.

The invention is further illustrated by way of the following example.

EXAMPLE

An improved barium salt of glucose was synthesized by the addition of equal volumes of 1M glucose and 2M barium chloride, shaking the solution for four days, then evaporating it slowly at 25 degrees Celsius or lower over sulfuric acid for about three weeks or more. This produced a water-insoluble salt for the matrix 13 applied as a first coating to the conductive substrate or electrode 17.

The hydrogel outer coating 15 for membrane matrix is a solution of the following composition:

| Reagents | Hydrogel solution (Coating 15) Name | Positive |
|---|---|---|
| I | 2-hydroxyethyl methacrylate (monome) | 5.0 m |
| II | N,N—dimethylamino ethyl methacrylate | 0.5 ml |
| III | Tetraethylene glycol dimethacryate | 0.2 ml |
| IV | Ethylene Glycol | 0.5 ml |
| V | Ammonium persulfate 0.4 g/mL | 1.00 ml |
| VI | Sodium Bisulfite .15 g/mL | 1.00 ml |
|  | Water | 4.5 ml |

The first four reagents are mixed. Ammonium persulfate is added as initiator and then sodium bisulfate as catalyst.

Polyvinyl chloride was separately dissolved in a minimal amount of cyclohexanone (5 gm PVC in 12 ml cyclohexanone). The barium salt solution and the polymer solution were then mixed in a 1:3 volume ratio. The tip of a platinum wire (0.257 mm in diameter) was then dipped twice into the mixed solution, and the solvent then evaporated by air drying at room temperature to form the membrane as a coating on the wire.

To form the positively charged, porous outer hydrogel coating 15 on the membrane, the membrane was then dipped into the hydrogel solution until entirely coated and set aside for about 12 hours to enable cross-linking of the hydrogel membrane.

The resulting membrane electrode was conditioned before use by soaking in $10_M{}^{-3}$ glucose solution for about a week at five degrees centigrade and then for two days at 37 degrees centigrade. The electrodes are also stored in the conditioning solution when not in use. The potential differences of the membrane electrode vs. a calomel reference electrode were determined in different concentrations of stagnant glucose solutions made with pH 7.4 phosphate buffer at 37 degrees C., using 600 mv bias.

(End of Example)

In both long-term and short-term tests, the membrane electrode was found to exhibit a current response which was linear with the logarithm of glucose concentration over the range of 40–200 mg percent.

x-ray diffraction and other testing of the electrode membrane of the invention has shown a substantially higher percentage of insoluble salt than in previous compositions and substantially reduced leaching of the barium component. The useful life for the improved membrane has been established as a matter of weeks or months instead of hours or days.

I claim:

1. An improved membrane electrode for measuring the concentration of a non-ionic species in an essentially aqueous medium comprising:
an electrically conductive substrate;

a first coating surrounding said substrate composed of a mixture of polymeric material, an anion exchange material, and a positively charged water-insoluble alkaline earth metal salt of said non-ionic species, and a hydrogel coating of material surrounding said first coating having a positive charge of sufficient potential to prevent leaching of the substantial amounts of the alkaline earth metal component of said salt.

2. The membrane electrode of claim 1 wherein said hydrogel coating comprises a mixture of a reagents including hydroxyethyl methacrylate, N,N dimethylamino ethyl methacrylate, tetraethylene glycol dimethacrylate, and ethylene glycol with an initiator material and a catalyst mixed in water.

3. The membrane electrode of claim 2 wherein the initiator material is ammonium persulfate and the catalyst is sodium bisulfate.

4. The membrane electrode of claim 1, wherein said non-ionic species is glucose.

5. The membrane electrode of claim 1, wherein said anion exchange material is a quaternary ammonium salt.

6. The membrane electrode of claim 4, wherein said alkaline earth metal is barium.

7. The membrane electrode of claim 5, wherein said non-ionic species is glucose, and said anion exchange material is a quaternay ammonium salt.

8. The membrane electrode of claim 1, wherein said conductive substrate is a noble metal.

9. The membrane electrode of claim 7, wherein said conductive substrate is in the form of a conductive wire.

10. The membrane electrode of claim 1 wherein the anion exchange material is present in amounts of from about 1 to about 25% of said membrane component, and wherein the molecular ratio of the anion exchange material to the water insoluble salt is from about 1:1 to about 3:1.

* * * * *